United States Patent [19]

Kerber

[11] 4,029,104
[45] June 14, 1977

[54] CALIBRATED LEAK BALLOON MICRO-CATHETER

[76] Inventor: Charles W. Kerber, 3728 SW. Beaverton Ave., Portland, Oreg. 97201

[22] Filed: Mar. 8, 1976

[21] Appl. No.: 664,503

[52] U.S. Cl. .............................. 128/348; 128/246; 128/349 B; 128/DIG. 16; 222/494; 128/2 A
[51] Int. Cl.² ........................................ A61M 25/00
[58] Field of Search ................ 128/DIG. 16, 349 B, 128/348, 351, DIG. 12, 349 BV, 350 R, 349 R, 350 V, 274, 245, 246, 225, 241, 129, 344, 2 A, 325; 138/109; 222/490, 494; 15/104.06 R

[56] References Cited

UNITED STATES PATENTS

| | | | |
|---|---|---|---|
| 397,060 | 1/1889 | Knapp | 128/349 B |
| 2,392,085 | 1/1946 | Ferrel | 222/490 X |
| 3,460,975 | 8/1969 | Stebleton | 128/348 X |
| 3,888,249 | 6/1975 | Spencer | 128/348 X |

OTHER PUBLICATIONS

"Intra-Arterial Instrumentation for Neurosurgery" by Alfred Luessenhop, M.D., *Dow Corning Bulletin* vol. 2, No. 3 p. 9.

*Primary Examiner*—Robert W. Michell
*Assistant Examiner*—Michael H. Thaler
*Attorney, Agent, or Firm*—Lee R. Schermerhorn

[57] ABSTRACT

This is an extremely small and flexible flow guided balloon catheter for use in small and tortuous blood vessels in body organs such as the brain or kidney, for diagnostic angiography. In order to attain such small size and extreme flexibility, a single lumen in the catheter tube serves the dual purpose of inflating the balloon and injecting a liquid into the blood vessel. This is accomplished by arranging the balloon to extend beyond the end of the catheter tube and providing a calibrated orifice in the distal end of the balloon to maintain inflation pressure in the balloon while the liquid is being discharged through the orifice.

6 Claims, 4 Drawing Figures

CALIBRATED LEAK BALLOON MICRO-CATHETER

BACKGROUND OF THE INVENTION

This invention relates to an extremely small and flexible flow guided balloon catheter for use in small and tortuous blood vessels in body organs such as the brain or kidney for diagnostic angiography.

Catheters have long been used for various purposes. One of the earliest types was the drainage catheter. These instruments were relatively large and stiff and presented no great problems either in manufacture or in manipulation in use. Later, vascular catheters were developed for use in the large veins and arteries. These also were relatively large in diameter and stiff enough to be advanced through a blood vessel by pushing on the proximal end. When such catheter was equipped with a balloon, it was not difficult to include a separate balloon inflation lumen in the catheter tube in addition to another lumen or lumens for diagnostic or treatment purposes.

More recently, flow guided catheters were developed having a balloon on the distal end which could be inflated to pull the catheter along by the flow of blood in an artery or vein. Such catheters had to be very flexible, but as long as they were used in the major veins and arteries they could still be large enough in diameter to accommodate a balloon inflation lumen, in addition to whatever lumens were required for diagnostic or treatment purposes. Thus, the use of the diagnostic angiography catheter as a therapeutic tool is becoming well accepted.

The conventional form of construction, however, is not capable of the size reduction necessary for use in the small and tortuous arteries in certain organs, such as the brain or kidney. And even if conventional catheters could be scaled down still further in size, other problems arise. The double or multiple lumen system becomes impractical because resistance to flow of fluid through a lumen increases inversely as the fourth power of the radius of the lumen, with a given length and fluid viscosity.

For the purpose of diagnostic angiography, it is necessary to inject a contrast agent or occluding material beyond the balloon. The lumen conveying such material must be of sufficient diameter to deliver the material at the distal end of the catheter within acceptable pressure limitations. This cannot be done in a double or multiple lumen system when the catheter tube is of very small diameter.

Objects of the invention are, therefore, to provide an improved catheter for diagnostic angiography, to provide an improved flow guided catheter for use in small and tortuous blood vessels, to provide a balloon catheter in which a material injected into a blood vessel is utilized to inflate the balloon and to provide a single lumen balloon catheter having a calibrated leak for injection.

SUMMARY OF THE INVENTION

In the present construction, a balloon is mounted to extend beyond the end of a single lumen catheter tube. The flexibility of the tube is such that the tube is limp, allowing the flow in a blood vessel to pull the catheter along through the vessel as a flow guided catheter. The balloon is inflated by liquid conveyed through the lumen for injection into the vessel. Balloon inflation pressure is maintained by a calibrated leak or orifice in the distal end of the balloon restricting the discharge of the liquid. The absence of a second lumen for balloon inflation allows the catheter to be of smaller size and more flexible than conventional diagnostic angiography catheters.

The invention will be better understood and additional objects and advantages will become apparent from the following description of the preferred embodiments illustrated on the accompanying drawing. Various changes may be made, however, in the details of construction and arrangement of parts and certain features may be used without others. All such modifications within the scope of the appended claims are included in the invention.

DESCRIPTION OF THE PREFERRED EMBODIMENTS

Figure 1:
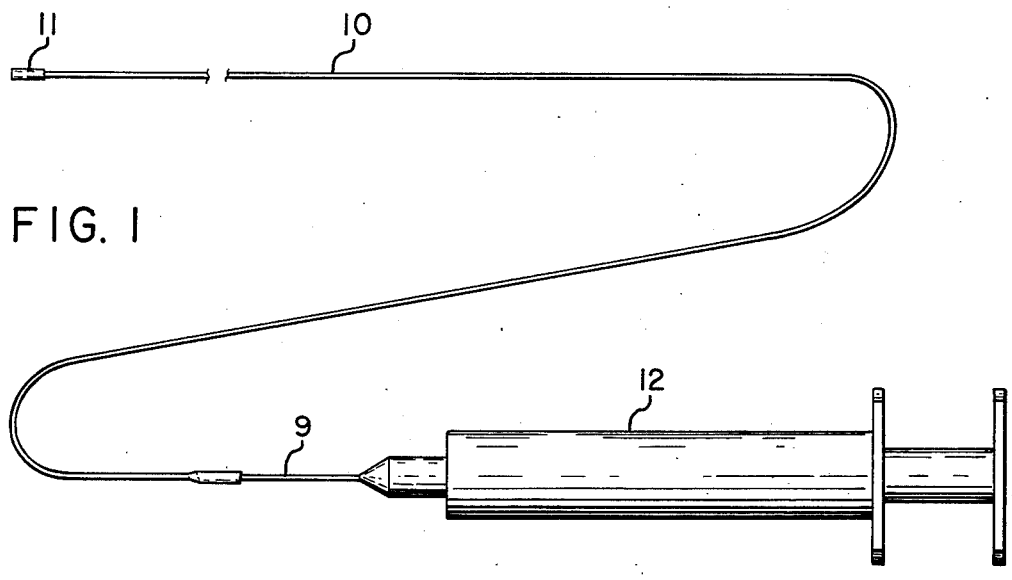
FIG. 1 is a view of a catheter embodying the invention, including a syringe for discharging a liquid through the catheter.

The catheter in FIG. 1 comprises a single lumen silicone rubber tube 10 having a silicone rubber balloon 11 on its distal end. In using the catheter, a syringe 12 is connected to its proximal end to force a liquid through the tube under pressure sufficient to inflate the balloon and inject the liquid into the blood vessel in which the catheter has been introduced. The liquid is injected from a restricted orifice in the end of the balloon which provides a calibrated leak capable of maintaining balloon inflating pressure in the liquid within the balloon.

Figure 2:
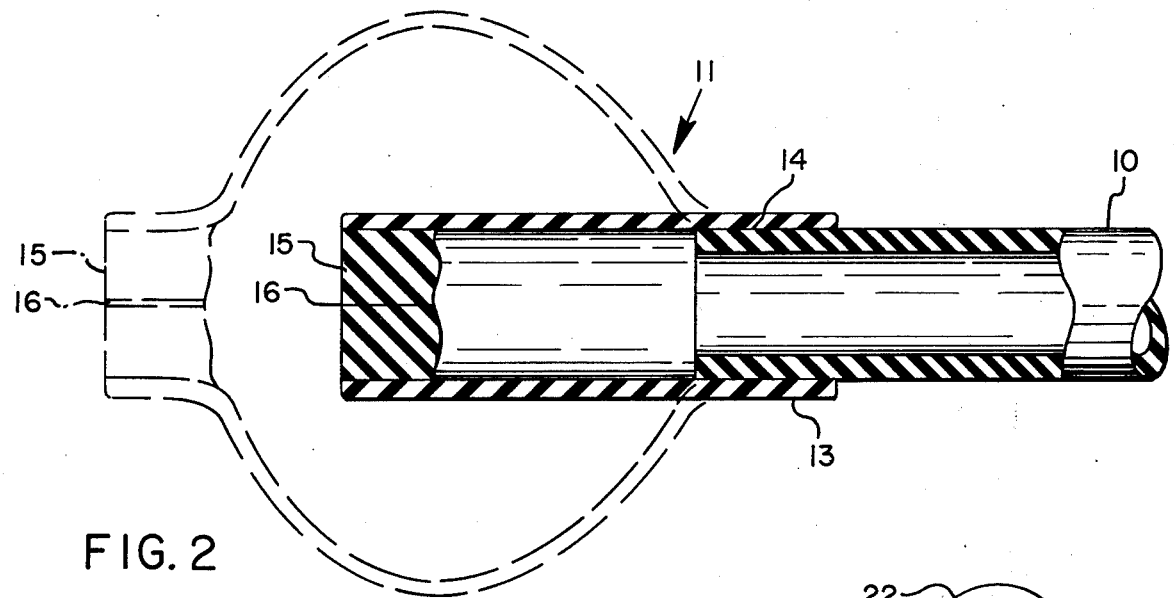
FIG. 2 is a greatly enlarged longitudinal sectional view of the distal end of the catheter showing the balloon construction.

As shown in FIG. 2, the balloon 11 comprises a silicone rubber cylinder 13 which is open at both ends. The proximal end of cylinder 13 receives the distal end of tube 10 and is bonded thereto by silicone rubber adhesive at 14. The distal end of cylinder 13 which extends beyond the end of tube 10 is closed by a plug 15. This plug is formed by depositing a cylinder of liquid silicone rubber in the distal end of cylinder 13 as shown. The liquid silicone bonds itself securely to cylinder 13.

After the plug 15 has cured, it is pierced with a needle or fine wire to form a discharge orifice 16. When the balloon is subjected to internal fluid pressure, it becomes distended between the end of tube 10 and plug 15 as indicated in broken lines and orifice 16 discharges fluid from the balloon.

In a typical catheter for the present purpose, the tube 10 has an inside diameter of 0.019 inch and an outside diameter of 0.034 inch and cylinder 13 is 0.125 inch long. The length of the expandable part of cylinder 13 between the end of tube 10 and plug 15 is 0.080 inch. This illustrates the minute size of the parts, but the dimensions are given merely by way of example and not for purposes of limitation.

Since no material is removed from plug 15 in the formation of orifice 16, the orifice will tend to close when the piercing instrument is removed as when a rubber nipple is pierced with a needle to form an orifice. In order to prevent the orifice from sealing itself closed, a piece of fine wire may be inserted and retained in orifice 16 until such time as the catheter is to be used.

Cylinder 13 may be formed by extrusion or by dipping a cylindrical mandrel into liquid silicone rubber, the cylinder being formed by the layer of liquid rubber which adheres to the mandrel. The mandrel is made of a material which does not readily bond to silicone rubber such as polyethylene or Teflon coated, polished aluminum whereby no mold release is required. Cylinder 13 is readily removed from the mandrel by brief immersion in a heavy organic solvent such as toluene. The toluene swells the cylinder 13 allowing the cylinder to be pulled from the mandrel.

Different techniques are available for introducing the catheter into the selected blood vessel. A stylet may be inserted in tube 10 rendering the tube stiff enough to be pushed into the vessel for a short distance.

Preferably, however, a larger catheter is first placed near the organ of interest using fluoroscopic control and percutaneous technique. The present catheter is coiled within a saline filled syringe and, with the balloon tip 11 protruding from the end of the syringe, the syringe is attached to the proximal end of the larger catheter. When the plunger of the syringe is depressed, the friction of the exiting fluid rapidly carries the present catheter well beyond the distal end of the larger catheter, the present catheter usually stopping and coiling within the artery at a point of arterial bifurcation. Then, the saline syringe is removed from the larger catheter and syringe 12, filled with a liquid to be injected into the artery, is connected with the proximal end of the present catheter by inserting the syringe needle 9 into catheter tube 10 as shown in FIG. 1.

The saline syringe technique for introducing catheter 10 into a blood vessel is illustrated and described in U.S. Pat. Nos. 3,703,174 and 3,826,256.

Inflation of balloon 11 in an artery by syringe 12 causes the blood flow to carry the balloon and the catheter distally in the artery. Final placement of the tip is effected by inflating balloon 11 varying amounts while at the same time manipulating the larger catheter. Syringe 12 may be filled with radio-opaque liquid for super selective angiography, or the syringe may be filled with suitable tissue adhesive for occlusion of the vessel distal to the balloon.

Orifice 16 is of specific caliber in relation to the properties of the liquid used in the catheter so that when the operator depresses the plunger of syringe 12 to inflate the balloon, a balance of forces exists allowing liquid to escape through orifice 16 while continuing to keep the balloon inflated. If higher flow rates become essential during the procedure, the balloon may be ruptured deliberately by applying sudden, excessive force on the plunger of syringe 12. The rather limited elasticity of silicone rubber is of advantage for this purpose.

The present single lumen catheter solves many problems for the angiographer. Conventional polyethylene catheters are difficult to pass through tortuous arteries or through arteries which change direction frequently. In this regard, balloon carried flow guided soft catheters excel, but the available small double lumen flow guided catheters are not practical when higher discharge rates are required because the lumens are too small. This problem is solved by the present single lumen catheter having a calibrated leak through its balloon tip. Both functions of balloon inflation and fluid delivery are carried out simultaneously, simply and with less difficulty in manufacture.

There is also another advantage in havng a balloon for catheter therapy, relating to blood flow control. High flow abnormalities such as arteriovenous malformations tend to carry an occluding adhesive beyond the desired occlusion point, allowing the therapeutic emboli to pass to the lungs. In the present catheter, the balloon stops blood flow through the abnormality long enough for the adhesive polymerization to take place. The catheter provides a rapid and reliable method of arterial occlusion. It is useful generally in the treatment of arteriovenous malformations and other vascular abnormalities.

Figure 4:
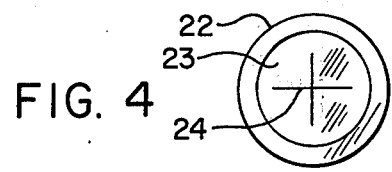
FIG. 4 is an end view taken on the line 4—4 in FIG. 3.
Figure 3:
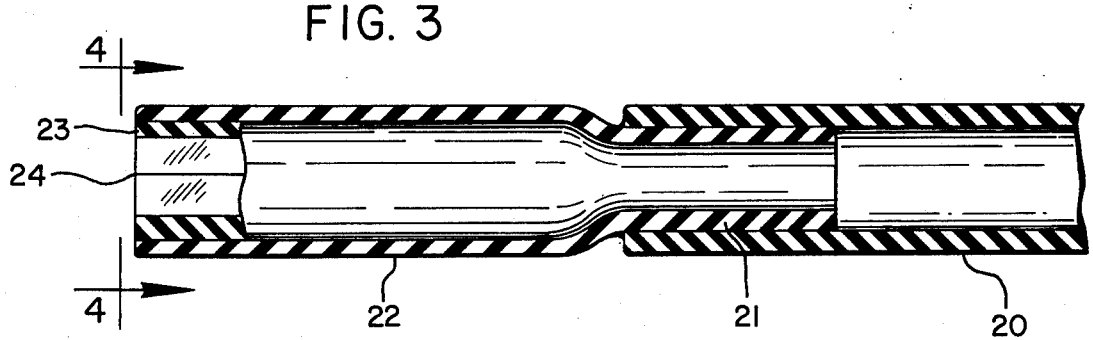
FIG. 3 is a view similar to FIG. 2 showing a modified form of construction.

The form of construction shown in FIGS. 3 and 4 is suitable for catheters having somewhat larger dimensions than those stated above. In this modification, the distal end of a single lumen silicone rubber tube 20 receives and is bonded to the reduced proximal end portion 21 of silicone rubber balloon 22. Balloon 22 may be formed by dipping a mandrel of corresponding shape in liquid silicone rubber as described above. The distal end of the balloon tube is open and receives a plug 23 of liquid silicone rubber as described in the first embodiment. After the plug has cured, an X-shaped orifice 24 is cut with a sharp instrument. The orifice remains closed or substantially closed until the liquid in the catheter is subjected to balloon inflating pressure by manipulation of the plunger in syringe 12 which is connected to the proximal end of tube 20, as explained in connection with FIG. 1.

The operation and use of the catheter in FIG. 3 are the same as described in connection with FIG. 1. The location of the neck of the balloon within the catheter tube in FIG. 3 causes the distension forces acting on the balloon to enhance the seal between the balloon and catheter tube, rather than tending to weaken the seal, when the tube is large enough to permit this arrangement.

What is claimed is:

1. A single lumen flow guided balloon catheter for use in small blood vessels in a body organ such as a brain or kidney, comprising a limp single lumen tube, a balloon having a proximal end connected to the distal end of said tube with the balloon extending beyond the end of said tube, said balloon comprising an imperforate hollow cylinder of silicone rubber, a deposit of liquid silicone rubber which cures to form a plug in the distal end of said cylinder, and a restricted orifice cut through said plug to discharge fluid from said lumen, said orifice maintaining sufficient back pressure in fluid supplied under pressure through said lumen to inflate the balloon for pulling the catheter through a blood vessel by the flow of blood in the vessel.

2. A catheter as defined in claim 1, said balloon being rupturable in said blood vessel by applying sudden excessive pressure to the fluid in said lumen, to produce a higher flow rate of said fluid into said vessel.

3. A catheter as defined in claim 1, the exterior surface of said tube being bonded to the interior surface of said cylinder.

4. A catheter as defined in claim 1, said cylinder having a proximal end portion of reduced diameter, and the interior surface of said tube being bonded to the exterior surface of said reduced end portion.

5. A catheter as defined in claim 1, said orifice having a circular cross section.

6. A catheter as defined in claim 1, said orifice having an X-shaped cross section.

* * * * *